US00PP19466P2

(12) United States Plant Patent
Sanders

(10) Patent No.: US PP19,466 P2
(45) Date of Patent: Nov. 18, 2008

(54) *IMPATIENS* PLANT NAMED 'IMTRASA'

(50) Latin Name: *Impatiens walleriana*
Varietal Denomination: Imtrasa

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/002,825

(22) Filed: Dec. 19, 2007

(51) Int. Cl.
*A01H 5/00* (2006.01)

(52) U.S. Cl. ..... Plt./318.7

(58) Field of Classification Search ..... Plt./318.7
See application file for complete search history.

*Primary Examiner*—Annette H Para
(74) *Attorney, Agent, or Firm*—S. Matthew Edwards

(57) ABSTRACT

A new *Impatiens* plant, characterized particularly as to novelty by a flat and strong outward spreading growth habit; freely branching with branches that tend to grow horizontally, resulting in a big and floriferous plant with large scarlet flowers.

1 Drawing Sheet

Latin name of the genus and species of the plant claimed: *Impatiens walleriana.*
Varietal denomination: 'Imtrasa'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar has a flat and spreading growing type, is floriferous with large scarlet flowers, and has attractive foliage.

The present cultivar originated from a cross-pollination made in 2003, of a proprietary *Impatiens walleriana* selection identified as 'T3103-1,' not patented, as the female, or seed parent, with a proprietary *Impatiens walleriana* selection identified as 'T2232-1,' not patented, as the male, or pollen parent.

The present cultivar has been repeatedly asexually reproduced by cuttings in Enkhuizen, Netherlands, in Angers, France, and in Gilroy, Calif., USA over a four year period. The new variety is stable and reproduces true to type in successive generations of asexual reproduction. It takes 6 to 8 weeks to produce a finished plant, depending on the temperature.

This new *Impatiens* plant is an annual in most climatic zones in the US, except in zones 9 and 10, where it is a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Impatiens.* The data which defines these characteristics were collected from asexual reproductions carried out in Enkhuizen, Netherlands. The plant history was taken on 27 week old plants blossomed under natural light in the field.

Color readings were taken in the office under ambient light. Color references are primarily to the R.H.S. Colour Chart of The Royal Horticultural Society of London.

Plants of the new *Impatiens* differ primarily from the plants of the female parent selection in the following characteristics:

Plants of the new *Impatiens* have bright scarlet flowers and a good trailing habit, whereas the plants of the female parent have red flowers.

Plants of the new *Impatiens* differ primarily from the male plant selection in the following characteristics:

Plants of the new *Impatiens* have bright scarlet flowers, whereas the plants of the male parent have carmine red flowers.

TABLE 1

DIFFERENCES BETWEEN THE NEW CULTIVAR 'IMTRASA' AND A SIMILAR CULTIVAR

| | 'Imtrasa' | 'Imtradared' (U.S. Serial No. 18,532) |
|---|---|---|
| Flower color: | Bright scarlet | Deep red |
| Leaf color: | Dark green | Dark green |
| Trailing habit: | Long trailing branches | Long trailing branches |

The family relationship is as follows:

The female parent line of 'Imtrasa' is 'RBGE 19821569'× 'J0475-2' crossed with line '0420,' line 'L0038' and line 'N0166.'

The male parent line of 'Imtrasa' is 'RBGE 19821569'× 'J0475-2' crossed with line 'K0086.'

The plant:
Parentage:
*Female parent.*—'T3103-1,' not patented.
*Male parent.*—'T2232-1,' not patented.

Propagation:
*Type cutting.*—Terminal cuttings.
*Time to initiate roots.*—10–12 days at 20° C.
*Time to produce a rooted cutting.*—4 weeks.
*Root description.*—Fine, fibrous, and white in color.

Plant description:
*General appearance.*—Makes long branches that tend to grow horizontally.
*Growth and branching habit.*—Freely branching habit, freely flowering, vigorous.
*Plant height.*—40 cm.
*Plant spread.*—100 cm.

Lateral branch description:
*Length.*—25–50 cm.
*Diameter.*—3–4 mm.
*Texture.*—Smooth, glabrous.
*Internode length.*—1–4 cm.
*Color.*—RHS N144A.

Foliage description:
*Arrangement.*—Alternate.
*Length, mature leaves.*—4.4 cm.
*Width, mature leaves.*—3.0 cm.
*Shape.*—Ovate.
*Apex.*—Acuminate.
*Base.*—Attenuate.
*Margin.*—Serrate.
*Texture.*—Smooth, glabrous.
*Venation pattern.*—Pinnate.
*Color young foliage, upper surface.*—RHS 137A.
*Color young foliage, lower surface.*—RHS 137C.
*Fully expanded foliage, upper surface.*—RHS 137A.
*Fully expanded foliage, lower surface.*—RHS 137C.
*Venation, upper surface.*—RHS 160A.
*Venation, lower surface.*—RHS 194B.
*Petiole, length.*—About 1 cm.
*Petiole, diameter.*—About 2 mm.
*Texture.*—Smooth, glabrous.
*Color.*—RHS 160A.

Flower description:
*Flower type and flowering habit.*—Single.
*Number of flowers per leaf axil.*—2–3.
*Number of flowers and flower buds per lateral branch.*—10.
*Flower position.*—Above and beyond the foliage and typically facing upwards and outward.
*Flower shape.*—Rounded, mostly flat.

Flowers lasting about 7–9 days on the plant depending on environmental conditions.
Flowers non persistent.
Flowers not fragrant.
Flowering indeterminate and continuous.
*Flowering season.*—Year round under greenhouse conditions. In the garden, flowering from spring until fall.
*Flower diameter.*—About 6 cm.

Flower buds:
*Rate of opening.*—From flower bud to fully open flower, typically about 6–8 days, depending on temperature.
*Bud length* (*at stage of showing color*).—About 1.5 cm.
*Bud diameter.*—About 0.6 cm.
*Bud shape.*—Ellipsoidal.
*Texture.*—Smooth, glabrous.
*Color, just before opening.*—RHS 45D.

Petals:
*Quantity.*—Single, five per flower, imbricate.
*Length of banner petal.*—About 2.5 cm.
*Width of banner petal.*—About 3.5 cm.
*Length lateral and basal petals.*—About 3.0 cm.
*Width lateral and basal petals.*—About 2.5 cm.
*Lateral and basal petal shape.*—Obovate.
*Banner petal shape.*—Broadly obcordate.
*Petal apex.*—Retuse to emarginate.
*Petal base.*—Attenuate.
*Petal margin.*—Entire.
*Petal texture.*—Smooth, satiny.
*Petal color.*—Upper surface when opening and fully opened: RHS 45A. Lower surface when opening and fully opened: RHS 40B.

Sepals:
*Lateral sepals.*—2.
*Shape.*—Ovate-lanceolate.
*Apex.*—Acute.
*Margin.*—Entire.
*Length.*—3–7 mm.
*Texture, upper and lower surface.*—Smooth, glabrous.
*Color of lateral sepals.*—RHS 146C.
*Spur.*—Length of spur: About 2.5 cm. Texture of spur: Smooth, glabrous. Aspect: Curved. Color of spur: RHS 184C.

Peduncles:
*Length of peduncles.*—About 2 cm.
*Diameter.*—0.1 cm.
*Aspect.*—About 45 degrees from the stem.
*Color.*—RHS 151A.
*Bracts.*—At least 2.
*Shape.*—Linear-lanceolate.
*Apex.*—Acute.
*Length.*—3–6 mm.
*Color.*—RHS 146C.

Reproductive organs:
*Androecium.*—Stamen number: Five fused at anthers, filaments free, hooded. Anther shape: Oval. Anther length: About 4 mm. Anther color: RHS 44A. Amount of pollen: No pollen.
*Gynoecium.*—Pistil number: One. Pistil length: About 5 mm. Stigma shape: Columnar, five segmented. Stigma color: RHS 72B. Style colour: RHS 44C. Ovary arrangement: Five celled. Ovary color: RHS 143B.

Seed development: Seed development has not been observed to date.
Disease/pest tolerance: No known susceptibility to disease or insects noted to date.

What is claimed is:

1. A new and distinct cultivar of *Impatiens* plant named 'Imtrasa,' as substantially illustrated and described herein.

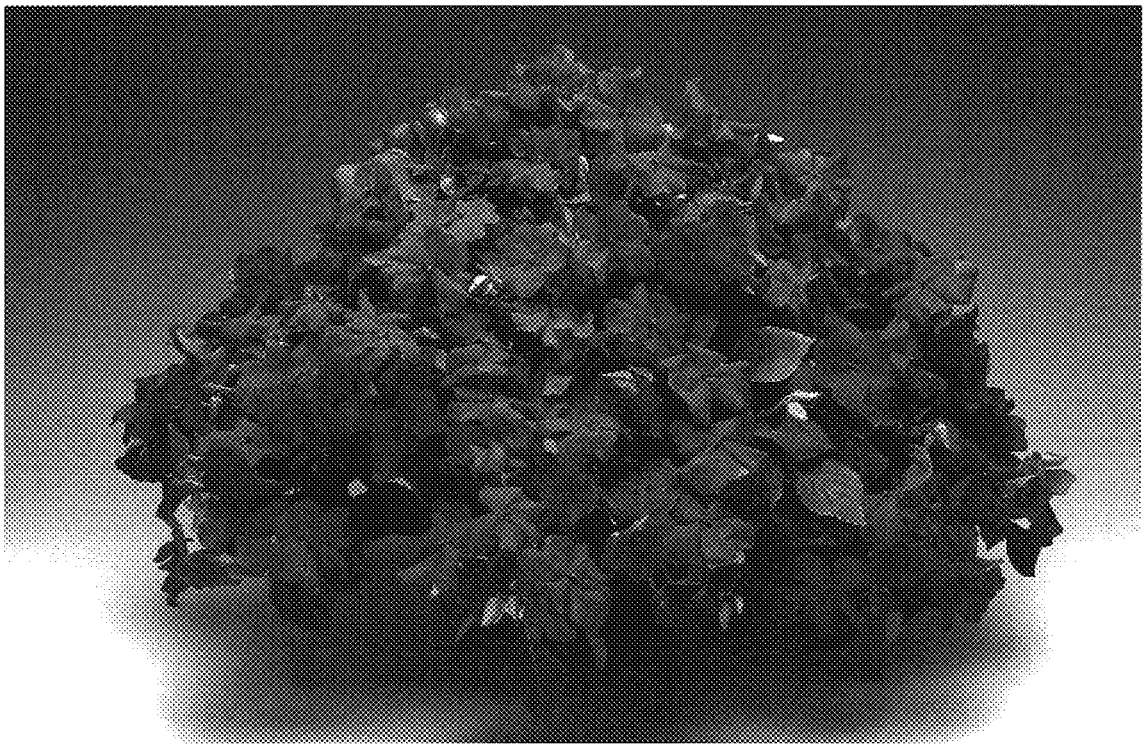

* * * * *